Figure 1:
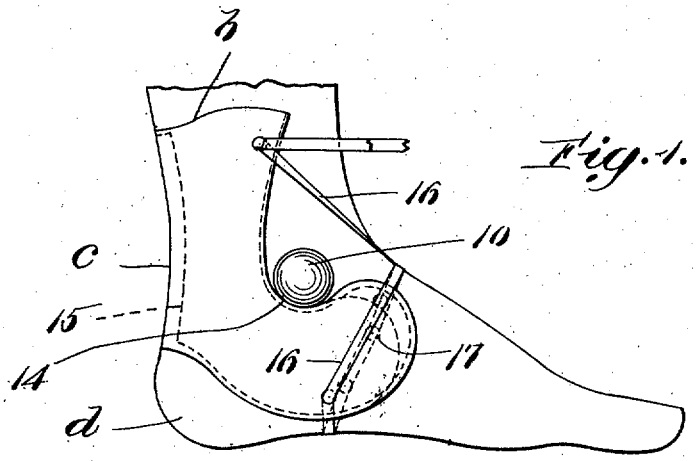

H. B. HAMILTON.

ANKLE SUPPORTER.

APPLICATION FILED JUNE 17, 1922.

Reissued Sept. 5, 1922. 15,446.

Inventor:
Harry B. Hamilton
by Jas. H. Chisholm
Atty.

Reissued Sept. 5, 1922. Re. 15,446

UNITED STATES PATENT OFFICE.

HARRY B. HAMILTON, OF NEW YORK, N. Y.

ANKLE SUPPORTER.

Original No. 1,397,095, dated November 15, 1921, Serial No. 444,126, filed February 11, 1921. Application for reissue filed June 17, 1922. Serial No. 569,172.

*To all whom it may concern:*

Be it known that I, HARRY B. HAMILTON, a subject of the King of Great Britain, and residing in the city, county, and State of New York (formerly of Boston, in the county of Suffolk and State of Massachusetts), have invented an Improvement in Ankle Supporters, of which the following description, in connection with the accompanying drawing, is a specification, like characters of the drawing representing like parts.

This invention relates to an ankle supporter, and has for its object to provide a simple and highly efficient device for this purpose. In accordance with this invention, the ankle supporter is provided with side members to support the thicker parts of the sides of the foot adjacent the ankle bone, and with filling members which project from the inner surfaces of said side members and are arranged thereon to cooperate with and support thinner parts of the foot adjacent the ankle bone, which thinner parts would not be supported directly by the side members if the filling members were omitted.

The filling members may be integral with the side members or stitched or otherwise fastened thereto, and it is preferred to provide each side member with a vertically arranged filling member to cooperate with the thin portion of the foot behind the ankle bone and above the heel, and also with a filling member laterally arranged with relation to the vertical filling member to cooperate with and directly support the thin portion of the foot below the ankle bone.

The particular features of the invention will be pointed out in the claims at the end of this specification.

Figure 1 is a side elevation of a foot provided with an ankle supporter embodying this invention.

Figure 2:
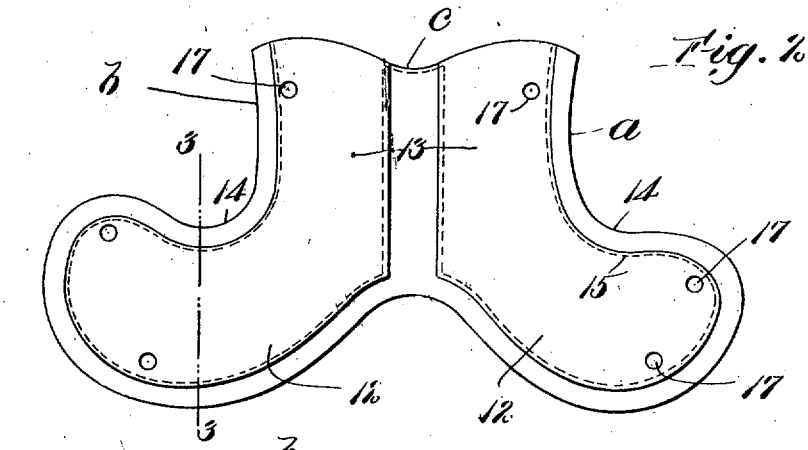
Figure 3:
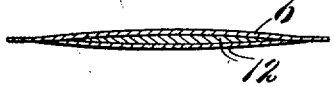

Fig. 2, a developed view of the supporter shown in Fig. 1, looking on the inside thereof, and Fig. 3, a section on the line 3—3, Fig. 2.

Referring to Fig. 2, *a*, *b* represent the side members of one form of ankle supporter embodying this invention. The side members *a*, *b* may be made of leather, felt, woven fabric or other suitable material, possessing the desired flexibility to enable it to be used without discomfort to the wearer.

The side members *a*, *b*, may be connected together at their rear or adjacent sides by a member *c*, which engages the rear portion of the foot above the heel *d* and forms a hinge for the side members *a*, *b*.

The side members *a*, *b* are designed to engage the thicker parts of the sides of the foot, but do not engage the thinner portions adjacent the ankle bone 10, and it is the purpose of this invention to provide a direct support for a thinner portion of the sides of the foot adjacent the ankle bone, and preferably for the thinner portion below the ankle bone and for the thin portion behind the ankle bone and above the heel *d*.

To this end, each side member is provided on its inner side with a filling member 12 to engage the thinner portion of the foot below the ankle bone, and with a filling member 13 to engage the thin portion of the foot behind the ankle bone.

The filling members 12, 13, may be individual members or they may be made as a continuous piece as herein shown. The filling member 12 is preferably curved to form with the member 13 a recess or socket 14 in its upper edge for the reception of the ankle bone. The filling members 12, 13, may be integral with the side members, or they may be separate therefrom and secured thereto by stitches 15 or otherwise.

The hinge member *c* enables the side members and their attached filling members to be moved toward and from each other to adjust the supporter to feet of different sizes.

The filling members may be composed of a plurality of pieces as represented in Fig. 3, and secured to the side members by the stitches 15, or they may be composed of a single piece integral with the side members or stitched thereto.

The filling members project from the inner surfaces of the side members and are located thereon so as to directly support the thinner portions of the sides of the foot adjacent to the ankle bone 10, and in the present instance the member 12 supports the thinner portion below the ankle bone and the member 13 supports the thin portion behind the ankle bone and above the heel, as represented in Fig. 1. The thin portions supported by the filling members would not be supported by the side members, if the filling members were omitted and it is in this respect that the present invention differs from and is superior to ankle supporters now generally used and known to me, inasmuch as the filling members afford a direct, firm, yet more or less flexible support for the thinner parts of the foot, which have not heretofore been supported.

In the present instance the supporter is shown as secured in position on the foot by a lacing 16, which is strung through eyes or openings 17 in the filling and side members. The eyes 17 are preferably arranged as shown so that the lacing when strung from one side member to the other will pass under the arch in the foot, and also across the instep and have its free ends tied together above the latter.

The side members of the supporter preferably have their lower edges curved upwardly toward the rear hinge portion *c* so as to enable the rear portion of the supporter to fit over and upon the heel and be supported thereby, after the manner shown in Fig. 1.

One of the filling members 12 and the side member *b* to which it is attached may and preferably will be made longer than the other and made of a greater curvature at its upper edge so as to conform to the difference in the size of the ankle bones, the longer filling member attached to the side member *b* cooperating with the smaller ankle bone on the outside of the foot. While it is preferred to provide the side members of the supporter with filling members which extend vertically and laterally, it is not desired to limit the invention in this respect, as beneficial results are obtained by the use of either alone.

One embodiment of the invention is herein shown, but it is not desired to limit the invention to the particular construction shown although it may be preferred.

Claims:

1. In an ankle supporter, in combination, a member to engage and support a thick portion of the side of the foot, and a filling member projecting from and beyond the inner surface of said member and arranged to engage and directly support a thinner portion of the foot adjacent to the ankle bone which is not directly supported by said member.

2. In an ankle supporter, in combination, side members connected together and capable of embracing the rear portion of the foot and engaging the thicker side portions thereof, and filling members projecting from and beyond the inner surfaces of said side members and arranged thereon to engage and support thin portions of the foot adjacent the ankle bone and not directly supported by said side members.

3. In an ankle supporter, in combination, side members connected together and capable of embracing the rear portion of the foot, and filling members projecting from and beyond the inner surfaces of said side members and comprising vertically arranged portions to engage with and support the thin part of the foot behind the ankle bone and portions which are extended laterally with relation to said vertical portions to engage with and support the thin part of the foot below the ankle bone.

4. In an ankle supporter, in combination, side members connected together and capable of embracing the rear portion of the foot, and filling members projecting from and beyond the inner surfaces of said side members and comprising vertically arranged portions to engage with and support the thin part of the foot behind the ankle bone, and curved portions extended laterally with relation to said vertical portions to engage with and support the thin part of the foot below the ankle bone.

5. In an ankle supporter, in combination, side members to engage and support the thicker portions of the foot, and filling members projecting from and beyond the inner surfaces of said side members and arranged thereon to engage with and support thin portions of the foot adjacent the ankle bone and not directly supported by the said side members.

HARRY B. HAMILTON